US00PP17231P2

(12) United States Plant Patent
Schoenmakers

(10) Patent No.: US PP17,231 P2
(45) Date of Patent: Nov. 21, 2006

(54) *FITTONIA* PLANT NAMED 'SNOW STAR'

(50) Latin Name: *Fittonia verschaffeltii*
Varietal Denomination: Snow Star

(75) Inventor: Kees Schoenmakers, Haaren (NL)

(73) Assignee: Schoenmakers Tropische Potcultures, Haaren (NL)

( * ) Notice: Subject to any disclaimer, the term of this patent is extended or adjusted under 35 U.S.C. 154(b) by 0 days.

(21) Appl. No.: 11/166,654

(22) Filed: Jun. 25, 2005

(51) Int. Cl.
*A01H 5/00* (2006.01)

(52) U.S. Cl. ..... Plt./373

(58) Field of Classification Search ..... Plt./373
See application file for complete search history.

(56) References Cited

U.S. PATENT DOCUMENTS

PP4,516 P * 4/1980 Engelmann ..... Plt./373
PP4,602 P * 10/1980 Cobia ..... Plt./373

OTHER PUBLICATIONS

UPOV ROM GTITM Computer Database, GTI Jouve Retrieval Software 2005/05 Citations for 'Snow Star'.*

* cited by examiner

*Primary Examiner*—Wendy Haas

(57) ABSTRACT

A new cultivar of *Fittonia* plant named 'Snow Star' that is characterized by small green and white leaves with green veins.

1 Drawing Sheet

Botanical classification: *Fittonia verschaffeltii.*
Variety denomination: 'Snow Star'.

BACKGROUND OF THE INVENTION

The present invention relates to a new and distinct cultivar of *Fittonia* plant botanically known as *Fittonia verschaffeltii* and hereinafter referred to by the cultivar name 'Snow Star'.

The new cultivar was discovered by the inventor in a cultivated area of Haaren, The Netherlands in 2001. 'Snow Star' was discovered as a naturally occurring whole plant mutation of *Fittonia verschaffeltii* 'White Anne' (not patented).

Asexual reproduction by terminal cuttings of the new cultivar 'Snow Star' was first done in 2001 in Haaren, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Fittonia* cultivar 'Snow Star'.

1. *Fittonia* 'Snow Star' exhibits small leaves.
2. *Fittonia* 'Snow Star' exhibits white and green leaves with green veins.

The closest comparison cultivar is the parent *Fittonia* 'White Anne'. The new cultivar 'Snow Star' is distinguishable from 'White Anne' by the following characteristics:

1. 'Snow Star' has leaf margins that are more wavy than 'White Anne'.

BRIEF DESCRIPTION OF THE DRAWING

The accompanying photograph illustrates the distinguishing traits of *Fittonia* 'Snow Star'. The plant in the photograph shows an overall view of a 12 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Fittonia* cultivar named 'Snow Star'. Data was collected in Haaren, The Netherlands from 12 week old greenhouse grown plants in 8.5 cm. containers. The time of year was Spring and the average temperature was 24 degrees Centigrade during the day and 22 degrees Centigrade at night. No photoperiodic treatments were used. Color determinations are in accordance with The Royal Horticultural Society Colour Chart 2001 edition, except where general color terms of ordinary dictionary significance are used. The growing requirements are similar to the species. 'Snow Star' has not been tested under all possible conditions and phenotypic differences may be observed with variations in environmental, climatic, and cultural conditions, however, without any variance in genotype.

Botanical classification: *Fittonia verschaffeltii* 'Snow Star'.
Use: Ornamental.
Parentage: 'Snow Star' is a naturally occurring whole plant mutation of *Fittonia* 'White Anne'.
Vigor: Moderate.
Growth rate: Moderate.
Growth habit: Broad spreading, upright.
Plant shape: Flattened globular.
Suitable container size: 8.5 cm. diameter container.
Height: Average 6.3 cm.
Width: Average 9.7 cm.
Hardiness: USDA Zone 10.
Propagation: Terminal cuttings.
Time to initiate roots: Approximately 21 days to produce roots on an initial cutting at 24 degrees Centigrade.

Time to produce a rooted cutting: Approximately 35 days to produce a rooted cutting at 24 degrees Centigrade.
Crop time: 12 weeks.
Root system: Fine and fibrous.
Stem:
*Branching habit.*—Moderately branching.
*Average number of lateral branches*—2.
*Pinching.*—Not needed.
*Lateral branch diameter.*—3 mm. in diameter.
*Lateral branch length.*—2.9 cm. in length.
*Lateral branch strength.*—Moderate.
*Stem color.*—144A to 144B.
*Pubescence.*—Dense, length 1.5 mm., color N155A.
*Internode length.*—1.9 cm. between nodes.
*Shape.*—Rounded, dull.
*Surface.*—Dull.
*Stem strength.*—Moderate.
Foliage:
*Leaf arrangement.*—Opposite.
*Compound or single.*—Single.
*Leaf shape.*—Obovate to broad obovate.
*Leaf apex.*—Rounded.
*Leaf base.*—Cordate.
*Leaf texture.*—Glabrous, slightly rugose, prominent venation.
*Leaf length.*—Average 4.5 cm. in length.
*Leaf width.*—3.6 mm. in width.
*Quantity of leaves per lateral branch.*—Average 4.
*Pubescence.*—Short hairs on margins, 0.5 mm. in length, N155A.
*Leaf margin.*—Repand and considerably wavy.
*Vein pattern.*—Pinnate.
*Young leaf color,* (*upper surface*).—145D with small dark spots, 145C, and green margins, 137A.
*Young leaf color,* (*lower surface*).—145C with darker venation, 145B, and green margins, 137A to 137B.
*Mature leaf color,* (*upper surface*).—137A to 139A.
*Mature leaf color,* (*lower surface*).—138A to 138B with darker margins, 137A to 137B.
*Vein color* (*upper surface*).—157D.
*Vein color* (*lower surface*).—145C.
*Leaf attachment.*—Petiolate.
*Petiole dimensions.*—Average 1.2 cm. in length, 2 mm. in diameter, 1.5 mm. in height.
*Petiole color.*—144B.
*Durability of foliage to stress.*—High.
Flowers: Flowers have not been observed.
Disease and insect resistance: Plants of the new *Fittonia* have not been observed for disease or insect resistance.

It is claimed:

1. A new and distinct variety of *Fittonia* plant named 'Snow Star' as described and illustrated.

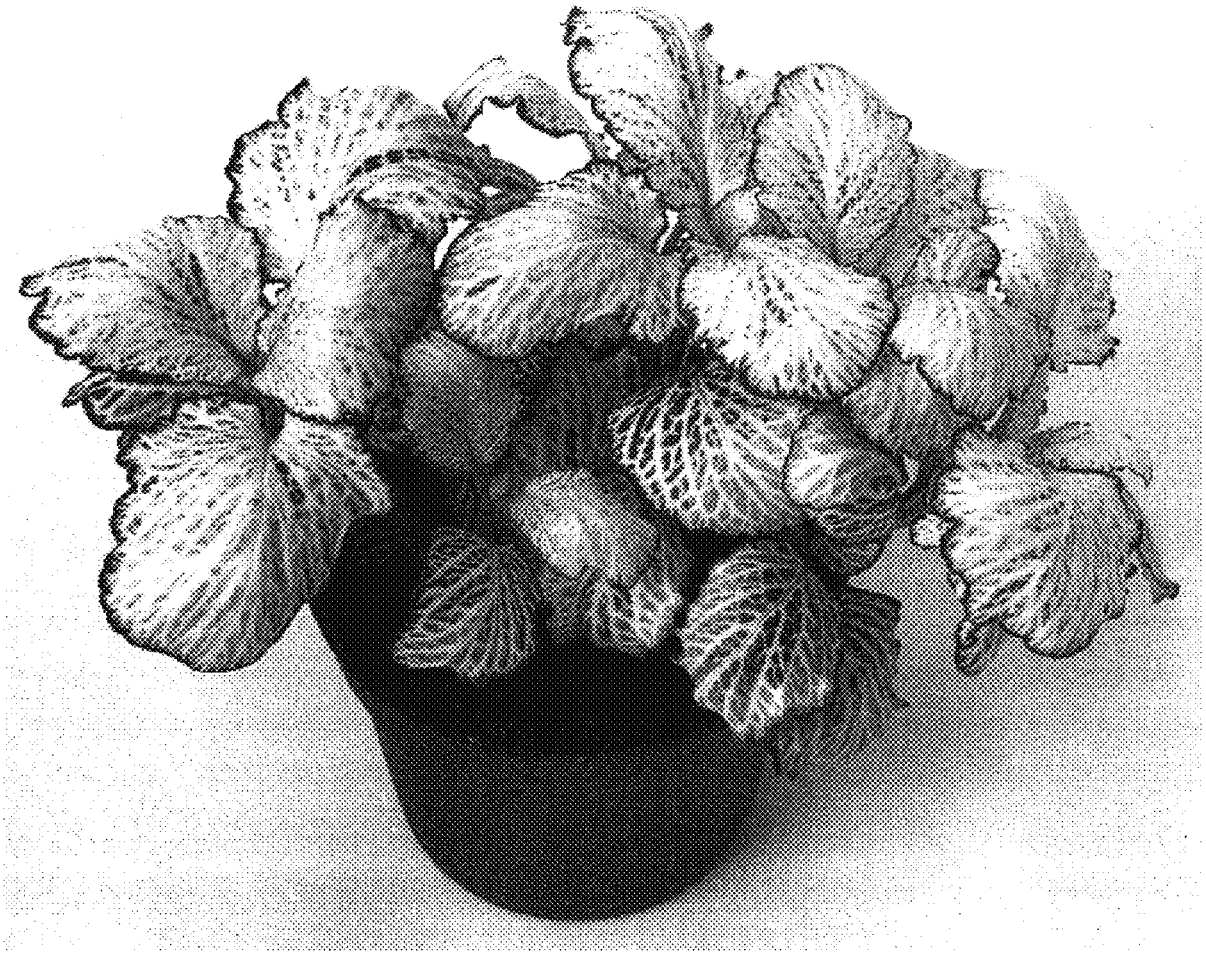

* * * * *